United States Patent [19]

Schiff et al.

[11] Patent Number: 4,921,809

[45] Date of Patent: May 1, 1990

[54] POLYMER COATED SOLID MATRICES AND USE IN IMMUNOASSAYS

[75] Inventors: Robert Schiff, Caldwell; Gary Lehnus, Blairestown, both of N.J.; Charles J. Wasserman, Muskego; Henrietta M. Garlock, Oconomowoc, both of Wis.

[73] Assignee: Findley Adhesives, Inc., Wauwatosa, Wis.

[21] Appl. No.: 105,136

[22] Filed: Sep. 29, 1987

[51] Int. Cl.$^5$ .............................................. G01N 33/545
[52] U.S. Cl. ........................................ 436/531; 422/73; 436/524; 436/532
[58] Field of Search ................ 436/531, 524, 532; 422/73

[56] References Cited

U.S. PATENT DOCUMENTS

| | | |
|---|---|---|
| 3,826,619 | 7/1984 | Bratu et al. |
| 3,876,504 | 4/1974 | Koffler ............................ 195/103 R |
| 4,001,583 | 10/1974 | Barrett ............................. 250/303 |
| 4,017,597 | 10/1974 | Reynolds ........................... 424/1.5 |
| 4,108,975 | 8/1978 | Hales ............................ 436/500 X |
| 4,147,752 | 1/1978 | Sunvaniemi ........................ 422/57 |
| 4,269,605 | 5/1981 | Dean ............................ 422/61 X |
| 4,410,634 | 11/1981 | Cooper et al. .................... 436/500 |
| 4,469,630 | 11/1983 | Flashner . |
| 4,525,456 | 11/1982 | Rohrbach ......................... 435/176 |
| 4,526,871 | 5/1981 | Avrameas et al. ................. 436/504 |
| 4,624,916 | 4/1984 | Shah et al. .......................... 435/7 |
| 4,629,692 | 12/1986 | Dean ........................... 436/518 X |
| 4,695,392 | 9/1987 | Whitehead ..................... 436/526 X |
| 4,719,176 | 1/1988 | Klotz ............................ 436/501 X |
| 4,753,983 | 5/1986 | Ngo ............................... 525/54.1 |

Primary Examiner—Barry S. Richman
Assistant Examiner—Jill Johnston
Attorney, Agent, or Firm—Ralph T. Lilore

[57] ABSTRACT

Certain polyethyleneimines are used to coat solid carriers used in immunoassays to improve the sensitivity of the assay over what is obtained without the coating. Use of the invention in enzyme immunoassays yields sensitivities equal to that of radioimmunoassays. A postcoating is also used after the solid carrier has had a layer of capture molecule applied and before the assay is performed, to improve even further the sensitivity, reliability and dynamic range of the assay results.

22 Claims, No Drawings

POLYMER COATED SOLID MATRICES AND USE IN IMMUNOASSAYS

BACKGROUND OF THE INVENTION

1. Field of the Invention

This invention relates to immunodiagnostic assay techniques and to methods for producing solid carriers which are useful in immunoassays. More particularly, it relates to a method for applying materials to solid carriers such as polystyrenes, polyethylenes and other plastics, woven or non-woven materials, cellulosics such as paper and wood or glass substances, so that the subsequent use of the solid carrier in an immunoassay results in higher sensitivities than are obtained without such material. Still more specifically, it relates to the introduction of a polymeric material onto a solid carrier to result in a carrier which gives very sensitive results upon the subsequent use of that material in an immunoassay measurement.

2. Description of Relevant Literature and Prior Art

Many differing prior art techniques have been used to conduct immunoassays. These techniques have utilized a wide variety of particular indicators, generally called markers, tags, tracers or labels, in the subsequent measurement of an analyte. In most immunoassays, there is a general requirement for the ultimate separation of a component which is labeled or tagged with an indicator from that same component in unlabeled form. A solid support carrier having the appropriate immunological materials attached is used to facilitate that separation.

The well-known sandwich assay for detecting or determining either an antigen or antibody in a sample is illustrative of immunoassays with which the present invention is useful. Assuming, for purposes of illustration only, that it is the antigen which is the analyte to be determined, a capture antibody is either adsorbed or covalently bonded to a solid carrier either directly or through an intermediate bridging layer. With regard to the latter, see U.S. Pat. No. 4,001,583 issued Jan. 4, 1977 to M. James Barrett relating to the use of glutaraldehyde as the means by which the bridging layer is covalently bound to subsequent proteinaceous materials. A biological liquid or a standard solution containing the antigen (or not containing it as the case may be) is incubated in the presence of the carrier/antibody composite for a suitable period of time during which the free antigen reacts with the capture antibody to form a complex on the composite. The complex is then contacted with a labeled component (usually the corresponding antibody) capable of binding to the sought antigen. This labeled component is generally described in the art as the "indicator antibody" because it contains the label which is subsequently used to measure the amount of labeled antibody bound to the antigen (or analyte) sought in the sample.

As indicated previously, many different indicators have been employed in the art. Tracers such as enzymes for enzyme immunoassay (EIA or ELISA) and radioactive labels for the so-called RIAs (radio immunoassays), and fluorescent and bioluminescent materials have all been employed. The art has discovered that for most analytes the best sensitivities are obtained generally from radio-immunoassays or fluorescent assays. Enzyme immunoassays give somewhat lower sensitivities limiting their use. From a practical point of view, those analytes that are present in very small quantities, say of the order of 10 nanograms and below, are most effectively measured utilizing radioimmunoassay as the optimal technique with fluorescent assays being suitable in some analytes. The art has not been favorably disposed to using enzyme immunoassays to detect these materials because of the difficulty of detecting concentrations below 10 nanograms. It would be very desirable indeed to provide a technique for obtaining sensitivities from an EIA or ELISA format which approach those of RIA, and indeed for even improving the sensitivities of RIA and other highly sensitive techniques.

One of the characteristics of the immunoassay techniques which tends to prevent obtaining sensitivities that are theoretically possible, relates to the ability of the tag to be detected at low levels in the presence of background activity caused by materials which are non-specifically bound to the capture molecule (antibody, antigen, etc.) or to the carrier itself. Since the RIA and fluorescent assays are inherently more sensitive than EIA, this drawback is less of a problem for them. But it can be seen that successful efforts to improve sensitivity would convert low sensitivity methods such as EIA or ELISA into those having sensitivities approaching or surpassing RIA. The art, as stated previously has attempted to improve this characteristic for all techniques by interposing an intermediate layer of a substance, such as glutaraldehyde, for example, onto the solid carrier prior to the application of the capture molecule. The effect of the glutaraldehyde placement is to bind the capture molecule covalently, i.e. more tightly and presumably in large quantities to the carrier. The latter characteristic would tend to obscure more of the carrier and make it unavailable for non-specific binding subsequently by the indicator molecule.

Similarly, other coating substances have been applied to the solid support in an effort to enhance attachment of the capture molecule. Bovine Serum Albumin has been used to form a physical absorbing layer while various polypeptides such as polyphenylalanine-lysine subsequently activated with glutaraldehyde, as shown in U.S. Pat. No. 4,657,873, have been used as plastic coating materials for covalent bonding to capture molecules.

SUMMARY OF THE INVENTION

We have found in the present invention that the interposition of a specific polymeric coating layer between a solid support carrier and the capture molecule serves to bind very large numbers of capture antibodies or other capture molecules (and therefore provides many more binding sites) and yields a composite which leads to greatly increased sensitivities in subsequent immunoassays. Since sensitivity is a function of, among other things, the number of binding sites actually affixed to the solid carrier and available for a subsequent reaction with the sought analyte, the present invention creates the opportunity for more sought analyte to be attached and therefore for more indicator molecules to be attached subsequently. At the same time, the present invention serves to supply a coating material which, while facilitating the binding of large numbers of capture molecules, also obscures the non-specific binding sites of the carrier.

The polymeric materials used as coating materials in the invention are extremely effective at capturing large amounts of proteinaceous material non-specifically. Therefore, in a preferred embodiment, although not absolutely necessary to gain the benefit of the first polymeric coat, a blocking agent or layer is applied after the capture molecule has been affixed to the polymeric coat but prior to reaction with the sought analyte. The purpose of this step is to block those polymeric binding sites on the polymeric coat that have not been covered by the capture molecule. The placement of the blocking layer then reduces the likelihood of non-specific binding of the indicator molecule to the polymeric coat. This enhances to a great degree the sensitivity characteristics which have already been greatly augmented by the ability of first polymeric layer to capture large amounts of the capture molecule.

DESCRIPTION OF SPECIFIC EMBODIMENTS

The present invention thus provides an improvement in the prior art processes and products for conducting those immunoassays wherein a capture molecule is present on a solid carrier, either directly or through an interposing layer of a material facilitating covalent or adsorptive bonding of the capture molecule to the layer, and wherein the resulting composite is contacted with a liquid in which sought analyte is thought to be present, and wherein the resulting composite is contacted with an indicator molecule comprising a labeled binding component capable of binding to the analyte, said improvement comprising providing on the surface of said solid support material, a polyethyleneimine (PEI) prior to the application of the capture molecule to the solid carrier. Most preferably, the improvement also comprises the provision of a blocking agent to the solid carrier after the capture molecule is attached to the PEI.

The invention in its most preferred form, comprises the application of the polyethyleneimine to the carrier before a covalent bonding material is affixed (if one is used), and in the ultimate preferred embodiment includes the subsequent attachment of the blocking agent prior tot he contacting of the carrier with patient's sample and after attachment of the capture molecule to the polyethyleneimine. In order to obtain the most benefit from the present invention, this latter mode is preferred.

The polyethyleneimines used in the present invention have the following general formulae:

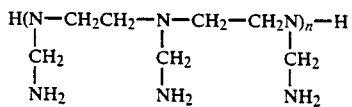

where n is an integer greater than 5, and

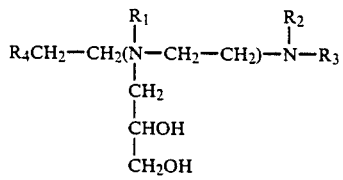

wherein $R_1$, $R_2$, $R_3$ and $R_4$ are hydrogen or the continuation of the polyamine chain provided that the molecular weight of the compound is up to 75,000 and preferably 15,000 to 45,000.

Preferred are the Polyethyleneimines of Formula I and of that category, those having a molecular weight in the range of 600 to 60,000 are suitable. We have found however, that a molecular weight in the range of 800 to 1800 produces highly preferred results. Unusually good results are obtained with a molecular weight of about 1200.

In applying the PEI to, for example polystyrene wells, as is normally done in the microtiter format preferred in this invention, a small quantity, for example about 200 microliters of a dilute solution of less than 10% and more suitably less than 1% solids of the PEI is conveniently applied to each well at room temperature and allowed to stand therein for about ten minutes. It is important to coat the surface of the well completely irrespective of the concentration of the PEI used. After that time, the liquids are emptied by decanting and the wells then allowed to dry overnight at from room temperature to 37° C.

We have found as a guide that the concentration of the PEI solution used is inversely related to the molecular weight so that as higher molecular weights are used more dilute concentrations are generally employed. In practicing the present invention, we have obtained best results with a PEI having a molecular weight of about 1200.

With regard to the carrier upon which the polyethyleneimine is deposited, a wide variety can be used. Although we prefer to use polystyrene, other carriers to which PEI attaches or adheres, can be employed. Other plastics, such as polyolefins of which the polyethylenes are illustrative, woven or non-woven materials, cellulosics such as paper and wood or glass substances, may be employed.

The materials referred to previously as those which facilitate covalent or adsorptive bonding of the capture molecule to the solid carrier are well known in the art. For example, glutaraldehyde has been used very extensively as such a material. In essence, any compounds which bind to PEI can be used as long as there are remaining functional groups for reaction with the antibody or antigen to be used as the capture molecule. For example, carbodiimides, periodates and any dialdehydes such as paraformaldehyde and the like may be used. For adsorptive binding, serum albumin has been used. As will be apparent to those skilled in the art, such materials that combine with or attach to any reactive amino or imino group of the PEI will be suitable. The particular material used is not part of the inventive concept of this invention but with the view of preparing a total, well-performing diagnostic kit, we prefer to use glutaraldehyde as the covalent bonding material. In the examples appearing hereinafter, we sometimes refer to the glutaraldehyde treatment as an "activation".

In utilizing the glutaraldehyde format, we prefer to use a dilute aqueous solution of glutaraldehyde of from about 0.01 to 0.1 percent by volume and to incubate the solution with the solid PEI coated carrier for a suitable period of time. Periods of from ¼ hour to 2 hours are suitable with ½ hour to 1 hour being preferred. Room temperature is suitable. After incubation, the carrier is then washed with distilled water. The glutaraldehyde apparently binds to the active primary nitrogen groups of the PEI leaving aldehyde groups to bind preferably with the amino groups of the capture molecule.

In carrying out the next step, that is in attaching the capture antibody to the glutaraldehyde covalent bonding layer (or directly to PEI), reaction conditions as are normally employed in the art will be suitable here. These are well known in the art. Suitably the capture molecule is solubilized in a suitable aqueous solution usually with a buffer and the reaction allowed to take place at a pH of from about 5–6. Concentrations of the order of 0.01 to 0.05 molar are suitable. We prefer to conduct the reaction at room temperature in the presence of small amounts of glycine (1–2 gm/liter) and mannitol 0.5 to 1.5 gms/liter).

Next the blocking agent, if desired, is applied. With regard to the blocking agent used in the invention, we have found that best results are obtained from a mixture of ovalbumin and dithiothreitol (DTT). In addition to the DTT and ovalbumin, we have also improved the results by adding additional, though optional, ingredients to varying degrees. For example, we can add lactalbumin, lactalbumin enzyme hydrolysate, para-aminobenzoic acid, or pyridoxyl phosphate, alone or in combination with one another. In general, the blocking agent is supplied in a dilute aqueous solution. The blocking agent itself (without regard to the aqueous vehicle) may be comprised of the following materials and concentrations by weights:

ovalbumin - up to 99%, preferably 45%–80%
DTT - 0.5–2%, preferably 0.7–1.5%
lactalbumin(or enzyme hydrolysate)-0–50% preferably 16–50%
para-aminobenzoic acid - 0–4% preferably 1.3–2.2%
pyridoxyl phosphate - 0–20% preferably 15–18%

The blocking agent is most conveniently supplied in the form of a dilute solution so that it can be conveniently applied to the PEI/capture molecule composite. Any mode of doing this which supplies sufficient blocker to block remaining active sites on the PEI which have not been consumed by the capture molecule (or glutaraldehyde) will be suitable. The actual amount applied will vary depending upon the polymer coat used, the quantity thereof and a variety of other factors. With PEI we have found that a concentration of from 0.5 to 2% by weight of the total blocker composition in the solution is suitable.

The application is conveniently done at room temperature or slightly elevated temperatures, preferably 37° C., with an incubation period of from ¼ hour to 1 hour. The resulting tray can then be dried, as by air drying, or by freeze drying under the usual lyophilization conditions. There is thus obtained from the foregoing description, a solid carrier having the PEI coating thereon and carrying the capture molecule. This composite is then useful in conducting immunoassays, such as a sandwich or competitive binding assay according to the preference of the user. These methods are well-known in the art. Polyethyleneimines useful in the present invention are known in the art and may be prepared by well-known methods.

The following examples are given to illustrate the invention.

EXAMPLE I

Application of Polyethyleneimine and Blocking Agent to the Substrate

The following is illustrative of the general procedure for applying the PEI and blockers to the solid carrier.

A. 200 microliters of the appropriate aqueous suspension of PEI (e.g. 10%, 1% or 0.005% solids, etc.) added to the wells of a polystyrene 96 well microtiter plate and allowed to stand for 10 minutes at room temperature. The wells were then decanted, inverted and tapped onto absorbent paper toweling to remove clinging drops of the PEI and then incubated at 37° C. overnight.

B. The dried plate obtained in Step A above is either used without further treatment or is next treated to activate the PEI and provide the basis for a covalent bonding bridge with capture antibody or antigen. In this regard, 200 microliters appropriate wells and incubated at room temperature for 30 minutes. The wells were then decanted, washed 3 times with distilled water, in tapped dry several times on paper toweling.

C. 200 microliters of the appropriate capture antibody solution was added to each well and incubated at 4° C. overnight. The capture antibody was made up in a glycine/mannitol buffer at pH 9.6.

D. The plates obtained from Step C were then post-coated with 200 ul of blocking agent per well, incubated at 37° C. for 30 minutes, decanted, tapped dry and washed once with distilled water and tapped dry.

The foregoing procedure in Step D was used in Examples II through VIII. Alternatively, the plates are frozen at −70° C. for one hour after the distilled water wash and then lyophilized at below 100 microns of Hg for about one hour. There are thus obtained from the above procedure, microtiter plates having capture antibody either covalently bound or adsorbed (depending on the procedure selected) onto the PEI, and protected by the blocking agent post-coat (or without post-coat in some later examples to show the effect thereof). These plates are then available for conducting the assays appropriate to the capture antibody.

EXAMPLE II

This example is illustrative of the assay technique employed using the plates obtained from Example I.

A. To the plate wells are added 200 microliters of calibrator, patient sample, or control depending on the purpose of the test. The plate is then incubated for 30 minutes at room temperature, washed three times with phosphate buffered saline with TWEEN 20, (PBS-T) decanted and tapped dry.

B. Thereafter, 200 microliters of the appropriate conjugate of the indicator molecule are added to the wells to be tested and incubated at room temperature for 30 minutes, washed three times with PBS-T and tapped dry.

C. To the plate obtained in B, 200 microliters of paranitrophenylphosphate (PNPP) substrate in the case of Examples III and IV and O-phenylenediamine (OPD) for all others, were added to each well at 10 second intervals and incubated at room temperature for 45 minutes. Absorbances were read at 10 second intervals at 405 nm for PNPP and 490–495 nm for OPD.

The procedure of Examples I and II were employed in the following examples using the materials indicated in each example. The results of each test are discussed.

EXAMPLE III

Materials:
Polymer - PEI molecular weight 1200, 10% solids
Capture antibody - Anti-Fab, affinity purified, obtained from Atlantic Antibodies, Scarborough, Me., used as a 1:500 aqueous dilution (0.05/25 ml)
Blocking Agent Post Coat - 0.5% ovalbumin, 1 millimole para-aminobenzoic acid, 0.5 millimole dithiothreitol all in a buffer of PBS pH 7.4
Analyte: IgG containing 25.95 mg/ml Conjugate: Alkaline Phosphatase - Fab'₂ to Fc in PBS-T diluted 1:5000

Microtiter plate 96 wells - Polystyrene

The analyte was serially diluted across 11 wells in the plate in 2-fold dilutions from 1:20,000 to 1:20,480,000 leaving the last well as a blank. The concentration of IgG in wells 7 through 11 were thus as follows:

7 - 20.8 ng/ml
8 - 10.4 ng/ml
9 - 5.2 ng/ml
10 - 2.6 ng/ml
11 - 1.3 ng/ml

A. Activation

When the above procedure was followed using the glutaraldehyde activation and the post-coating procedures, reliable absorbance readings were obtained up to well #8 indicating a sensitivity of at least 10.4 ng/ml.

B. No Activation

When the above procedure was employed omitting the glutaraldehyde activation step, reliable absorbance readings were obtained up to well #8 indicating no difference in the procedure between activation and no-activation.

C. 1% Solids PEI

When the procedure of A above and B above were separately followed using a 1% solids suspension of PEI, the sensitivity increased to detection at well #10, i.e. to at least 2.6 ng/ml, thus indicating better results from a lower dilution of applied PEI than from a higher one.

D. Control - No PEI

When the procedure of A above was followed omitting the application of the PEI to the plate, reliable absorbance readings could only be obtained up to well #7 i.e. a concentration of 20.8 ng/ml.

This example shows clearly the benefit of the PEI layer when compared to the control and shows that lower dilutions by PEI provide very good sensitivities in this particular experiment. No difference was noted between the "activation" and "non-activation" procedures.

EXAMPLE IV

Materials:

Same as in Example III A except that Anti-IgM is used as the capture antibody and an IgM standard of 261 mg/dl is used as the analyte. The concentration of IgM in wells 4–11 were as follows:

4 - 332.8 ng/ml
5 - 166.4 ng/ml
6 - 83.2 ng/ml
7 - 41.6 ng/ml
8 - 20.8 ng/ml
9 - 10.4 ng/ml
10 - 5.2 ng/ml
11 - 2.6 ng/ml

A. IgM instead of IgG as analyte - Activated PEI

When the procedure of Example III A is followed using the above materials, reliable absorbance readings were obtained through well #6, i.e. a concentration of 83.2 ng/ml.

B. IgM instead of IgG as analyte - No-Activation of PEI

When the procedure of Example III B is followed using the above materials, reliable absorbance readings were obtained through well #8, i.e. a concentration of 20.8 ng/ml.

C. 1% PEI Solids

1. Activation - When the procedure of Example III C is followed using the above materials, reliable absorbance readings were obtained through well #9, i.e. an IgM concentration of 10.4 ng/ml.

2. No-Activation - When the procedure of Example III C is followed using the above materials, reliable absorbance readings are obtained through well #6, i.e. a concentration of 83.2 ng/ml.

This example indicates the desirability of having an activation step where larger molecules such as IgM are being detected and lower concentrations of PEI are used.

D. When the control procedure of Example III D was followed using the above materials, reliable absorbances were obtained up to well #6 in one experiment and up to well #7 in another for sensitivities of 83.2 ng/ml and 41.6 ng/ml respectively.

EXAMPLE V

This example shows the effect of using higher molecular weight PEI's and variable concentrations of the polymer during the application stage (Step A, Example I)

Materials

PEI - 1200 molecular weight - variable % solids
PEI - 50,000 molecular weight
SC86X - Polymer of Formula II, mol.wt. 15,000–45,000 obtained from Thiokol Chemical Products.

Capture Antibody - anti-HCG monoclonal, 1:1000 dilution.

Conjugate - Anti-beta HCG monoclonal horseradish peroxidase conjugate.

Analyte - Beta HCG 8400 IU. standard obtained commercially and diluted to 0, 4.2, 10.5 and 420 milliI.U./ml in PBS.

The general procedure of Example III was followed using the variable % solids indicated in the table with activation. The table below summarizes the absorbances obtained for the various concentrations of solids and for the four levels of Beta HCG concentration.

TABLE I

| Std | PEI-12 | | | PEI-50 | | | | SC86X | | | | |
|---|---|---|---|---|---|---|---|---|---|---|---|---|
| MIu/ml | .01% | *.005% | .0025% | .01% | *.005% | .0025% | .00125% | .01% | *.005% | .0025% | .00125% | Polystyrene |
| 420 | 1.079 | 1.097 | .986 | 1.004 | 1.185 | 1.069 | .851 | .540 | .557 | .244 | .222 | .208 |
| 10.5 | .095 | .103 | .091 | .094 | .084 | .074 | .076 | .063 | .061 | .037 | .029 | .047 |
| 4.2 | .049 | .044 | .042 | .046 | .041 | .039 | .041 | .044 | .039 | .031 | .026 | .028 |
| Zero | .027 | .021 | .022 | .031 | .025 | .018 | .019 | .032 | .026 | .021 | .024 | .023 |

From the above table it will be noted that:

A. Reliable absorbance readings are obtained down to a beta-HCG concentration of 4.2 mIU using lower concentration of PEI-1200 than shown in the previous examples.

B. Similar readings are obtained for the higher molecular weight polymers with the exception of the very dilute concentration of Polymer SC86X.

C. The control (Polystyrene alone-no PEI) is readily distinguishable from the readings at the 10.5 beta HCG concentrations for polymer concentrations above 0.005% solids.

EXAMPLE VI

Materials - Same as in Example III. This example is intended to show the effect of the blocking agent with and without Lactalbumin (or the enzymatic hydrolyzate) The blocking agent was the same as in Example III except that varying amounts of Lactalbumin (LA) and Lactalbumin Enzymatic Hydrolyzate (LEH) were added to determine the effect on sensitivity.

Following the procedure set forth in Example III A, three levels of LA and LEH as shown on the Table were employed in the blocking agent shown below.

Blocking Agent - 0.5% ovalbumin, 1 millimole para-aminobenzoic acid, 0.5 millimole dithiothreitol, The results are shown below in Table II

|  | 420 mIU | 10.4 mIU | 4.2 mIU | Blank |
|---|---|---|---|---|
| (a) Blocking Agent with Lactalbumin at 0.25% | 1.334 | 0.143 | 0.074 | 0.013 |
| (b) Blocking Agent with Lactalbumin at 0.125% | 1.292 | 0.150 | 0.072 | 0.003 |
| (c) Blocking Agent with Lactalbumin at 0.01% | 0.946 | 0.201 | 0.114 | 0.061 |
| (d) Blocking Agent with Lactalbumin at 0.00% | 1.124 | 0.319 | 0.266 | 0.263 |
| (e) Blocking Agent with LEH* at 0.0078% | 1.387 | 0.323 | 0.267 | 0.214 |
| (f) Blocking Agent with LEH* at 0.1% | 1.371 | 0.336 | 0.223 | 0.187 |
| (g) Blocking Agent with LEH* at 0.5% | 1.417 | 0.240 | 0.181 | 0.099 |

*LEH = Lactalbumin Enzymatic Hydrolysate

As can be seen, while the blocking agent without lactalbumin gives suitable results, i.e. a sensitivity of at least 10.4 mIU, the presence of Lactalbumin promotes a sensitivity detection of at least 4.2 mIU.

Similarly, LEH enables better sensitivity detection at suitable LEH concentrations of 0.1% and 0.5%.

EXAMPLE VII

The general procedure of Example V is followed except that (1) following the addition of the standard, the conjugate is added immediately and the resulting mixture incubated in presence of the capture antibody for 15 minutes at room temperature.

(2) The blocking agent was
5% ovalbumin
0.1% lactalbumin
1 millimole PABA
0.5 millimole DTT
and the pH of the blocking agent application was 6.5, 7.4 or 9.8.

Reliable absorbance readings were obtained at sensitivities of 1:5,120k (1.7 milliIU) at pH's of 6.5 and 7.4. Under the conditions and with the materials used in this example, a pH of 9.8, however, did not produce suitable results.

EXAMPLE VIII

The general procedure of Example VII was followed in a competitive binding assay for Digoxin, except that the following materials were used:
Capture Antibody - digoxin monoclonal antibody
Blocking agent of Example-VI (g)
Antigen - 4 ng/ml standard digoxin serially diluted to 0.0039 ng/ml.
Conjugate - Digoxin antigen labeled with horse radish peroxidase enzyme
0.25% solids PEI-12.(molecular weight 1200)

Using the above procedure, reliable absorbance readings were obtained at the indicated sensitivities for the following experimental variables:
(a) Activated PEI - Sensitivity of 0.015 ng/ml
(b) non-activated - PEI - Sensitivity of 0.5 ng/ml
(c) Polystyrene well alone (control)-Sensitivity of 1-4 ng/ml.

EXAMPLE IX

The general procedure of Example V is followed except that:

(1) The alternative freeze drying step described in step D of Example I was used following the application of the post coat.

(2) The blocking agent was:
(0.5% ovalbumin
(0.5% lactalbumin enzyme hydrolysate
(1 millimole PABA
(0.5 millimole DTT PEI = 1200 molecular weight, 0.005% solids and the pH of the blocking agent application was 7.4.

Analyte - Beta HCG from human patient serum.

Standards - Beta HCG human serum-based standards obtained commercially from Medix Biotech Inc., Foster City, Calif., at concentrations of 0, 5, 50, 200 milliIU used to prepare standard curves.

Enzyme substrate-orthophenylenediamine.

The specific procedure was as follows:

(1) With strips in plate holder and beginning with A-1 (top left); we dispensed the Standards in duplicate e.g., A-1, B-1=0 mIU Standard; C-1, D-1=5 mIU Standards and so on. We Dispensed 100 ul of each undiluted Standard into the Standard wells and 100 ul of patient sera into the remaining wells.

(2) After all Standards and patient samples were added, we immediately added 100 ul of reconstituted conjugate into the wells using a single or multitip pipettor. After conjugate is dispensed into the wells, we swirled the plate gently and incubated for 15 minutes at 20°-25° C.

(3) After incubation, we discarded the sample (or standard)/ conjugate solution, washed the wells with distilled/deionized water and discarded the wash. We repeated the procedure 3 more times. Excess water was removed by inverting and tapping the plate on a paper towel.

(4) Employing freshly prepared substrate solution, we dispensed 200ul of substrate into all wells at a constantly timed interval e.g., one strip every 10 seconds.

(5) After the substrate was added to all wells, we swirled gently and incubated at 20°-25° C. for 30 minutes.

(6) After incubation we read the absorbance of the wells at 490-492 nm., blanked the instrument on the A-1 (0 mIU standard) well and read the remaining wells at the same timed intervals that the substrate was added.

(7) After all wells were read, we plotted the absorbance of the Standards (Y axis) versus their concentration (X axis) and constructed a "best-fit" line with a straight edge.

(8) We determined the concentration of the patient samples from the standard curve by finding the absorbance on the Y axis and reading the concentration from the X axis where it intersects the standard curve.

The patient samples were unknowns containing beta HCG. The results of the tests were compared to RIA results on the same unknowns and found to correlate very well. The table below shows the results obtained on samples having less than 50 milliIU by RIA analysis.

| SAMPLE NUMBER | MilliIU by RIA | MilliIU by EXAMPLE IX |
|---|---|---|
| 16 | 46 | 46 |
| 22 | 11 | 16 |
| 25 | 22 | 12 |
| 28 | 14 | 17 |
| 35 | 32 | 22 |
| 36 | <5 (neg) | 1 (neg) |
| 53 | <5 (neg) | 1.4 (neg) |
| 54 | <5 (neg) | 1.3 (neg) |
| 55 | <5 (neg) | <5 (neg)* |
| 61 | 26 | 31 |

*Upon repeat (first reading was 34)

What is claimed is:

1. In an immunoassay solid support carrying a capture molecule directly or through an interposing layer of a material facilitating covalent or adsorptive bonding of the capture molecule to the support, the improvement which comprises a layer of a polyethyleneimine on said support intermediate said support and said capture molecule and wherein there is a blocking agent present on the polyethyleneimine capture antibody composite comprising a mixture of ovalbumin and dithiothreitol.

2. The immunoassay solid support of claim 1 wherein the capture molecule is an antibody or antigen.

3. The immunoassay solid support of claim 2 wherein the polyethyleneimine has a molecular weight of from 600 to 60,000.

4. The immunoassay solid support of claim 3 wherein the solid support is polystyrene.

5. The immunoassay solid support of claim 4 wherein said interposing layer is glutaraldehyde.

6. The immunoassay solid support of claim 4 wherein the polyethyleneimine has a molecular weight of 800 to 1800.

7. The immunoassay solid support of claim 1, wherein the blocking agent additionally contains one or more of lactalbumin, lactalbumin enzymatic hydrolyzate, para-aminobenzoic acid and pyridoxyl phosphate.

8. The product of claim 7 wherein the capture antibody is for beta-HCG.

9. In a method for producing a solid support substrate useful in performing an immunoassay wherein a capture molecule is attached to said solid support directly or through an interposing layer of a material facilitating covalent or adsorptive bonding of the capture molecule to said layer, the improvement which comprises applying a layer of a polyethyleneimine onto said support intermediate said support and said capture molecule and then treating the resulting product with a mixture comprising ovalbumin and dithiothreitol sufficient in amount to provide a blocking layer of the polyethyleneimine layer.

10. The method of claim 9 wherein the capture molecule is an antibody or antigen.

11. The method of claim 10 wherein the polyethyleneimine has a molecular weight of from 600 to 60,000.

12. The method of claim 11 wherein the solid support is polystyrene.

13. The method of claim 12 wherein said interposing layer is glutaraldehyde.

14. The method of claim 13 wherein the support layer is polystyrene.

15. The method of claim 13 wherein the capture antibody is for beta-HCG.

16. The method of claim 13 wherein the blocking mixture further comprises one or more of the following: para-aminobenzoic acid, lactalbumin, enzymatic hydrolysate of lactalbumin, and pyridoxyl phosphate.

17. The method of claim 16 wherein the blocking mixture comprises, by weight, 45-80% ovalbumin, 0.7-1.5% dithiothreitol, 16-50% lactalbumin or lactalbumin enzymatic hydrolysate, 1.3-2.2% para-aminobenzoic acid, and 15-18% pyridoxyl phosphate in aqueous solution.

18. In a method for conducting an immunoassay wherein a solid support carrier having a capture antibody attached thereto either directly or through an interposing layer of a material facilitating covalent or adsorptive bonding of the capture antibody to the layer, and said antibody is contacted with a liquid in which the presence and/or concentration of an antigen is to be determined, and said contacted antibody is contacted with a labeled form of a binding partner of said antigen and the extent of attachment of such labeled form is measured to measure the presence and/ or concentration of said antigen, the improvement which comprises applying a layer of a polyethyleneimine to said support carrier intermediate said support and said capture antibody and then treating the resulting product with a mixture comprising ovalbumin and dithiothreitol sufficient in amount to provide a blocking layer on the polyethyleneimine layer.

19. The method of claim 18 wherein the polyethyleneimine has a molecular weight of from 600 to 60,000.

20. The method of claim 19 wherein the solid support is polystyrene.

21. The method of claim 20 wherein a layer of glutaraldehyde is applied to said layer of polyethyleneimine to facilitate covalent bonding of the capture antibody thereto.

22. The method of claim 21 wherein the support layer is polystyrene.

* * * * *